US012746355B2

(12) United States Patent
Lee et al.

(10) Patent No.: US 12,746,355 B2
(45) Date of Patent: Sep. 29, 2026

(54) INTELLIGENT EXHALED SPUTUM-SUCTION AND INHALED OXYGEN-SUPPLY DEVICE

(71) Applicant: METABRAIN TECHNOLOGY PTE. LTD., Singapore (SG)

(72) Inventors: Shin-Da Lee, Taichung (TW); Bor-Tsang Wu, Tainan (TW)

(73) Assignee: METABRAIN TECHNOLOGY PTE. LTD., Singapore (SG)

( * ) Notice: Subject to any disclaimer, the term of this patent is extended or adjusted under 35 U.S.C. 154(b) by 588 days.

(21) Appl. No.: 18/349,546

(22) Filed: Jul. 10, 2023

(65) Prior Publication Data

US 2025/0018137 A1 Jan. 16, 2025

(51) Int. Cl.

*A61M 16/00* (2006.01)
*A61B 34/30* (2016.01)
*A61M 16/04* (2006.01)

(52) U.S. Cl.

CPC ...... *A61M 16/022* (2017.08); *A61M 16/0009* (2014.02); *A61M 16/024* (2017.08); *A61M 16/0463* (2013.01); *A61B 2034/301* (2016.02); *A61M 2016/0027* (2013.01); *A61M 2016/0039* (2013.01)

(58) Field of Classification Search

CPC ...................... A61M 16/0009; A61M 16/0463
See application file for complete search history.

(56) References Cited

U.S. PATENT DOCUMENTS

2004/0216743 A1* 11/2004 Orr .................. A61M 16/0093 128/205.12
2021/0228289 A1* 7/2021 Rohr Daniel ........ A61B 1/0016
2021/0379275 A1* 12/2021 Pham ................ A61M 16/0477
2022/0125539 A1* 4/2022 Inouye .................. A61B 34/71
2023/0109332 A1* 4/2023 Phillips ............ A61M 16/0051 128/200.24

FOREIGN PATENT DOCUMENTS

TW I772217 B 7/2022
WO WO-2024221587 A1 * 10/2024 ........... A61B 1/2676

* cited by examiner

*Primary Examiner* — Bradley H Philips
(74) *Attorney, Agent, or Firm* — MUNCY, GEISSLER, OLDS & LOWE, P.C.

(57) ABSTRACT

An intelligent exhaled sputum-suction and inhaled oxygen-supply device is provided, including a sputum-suction and oxygen-supply tube unit, a gas-regulating unit and a control unit. The sputum-suction and oxygen-supply tube unit includes a major oxygen-supply tube and a major sputum-suction tube, and the gas-regulating unit includes an oxygen-supply module supplying oxygen to the major oxygen-supply tube, a sputum-suction module, and a respiration sensor configured to sense a breathing state of a patient. The control unit is electrically connected with the sputum-suction module and the respiration sensor, and the control unit controls the sputum-suction module to draw gas from the minor sputum-suction tube when the respiration sensor senses that the patient is in an exhalation state so as to simplified the operation processes.

9 Claims, 8 Drawing Sheets

INTELLIGENT EXHALED SPUTUM-SUCTION AND INHALED OXYGEN-SUPPLY DEVICE

BACKGROUND OF THE INVENTION

Field of the Invention

The present invention relates to an intelligent exhaled sputum-suction and inhaled oxygen-supply device.

Description of the Prior Art

Please refer to FIG. 1, showing a conventional sputum-suction device 11. The conventional sputum-suction device 11 is operated by an operator to be connected with a tracheostomy tube of a patient for oxygen-supply and sputum suction. The conventional sputum-suction device 11 includes an outer tube 111, an oxygen-supply tube 112 communicated with the outer tube 111 and a suction tube 113 penetrating through the outer tube 111.

The outer tube 111 is inserted into the tracheostomy tube of the patient to supply oxygen to the patient through the oxygen-supply tube 112, and then the suction tube 113 is inserted into the tracheostomy tube through the outer tube 111 for sputum suction.

However, during sputum suction, the operator has to observe the blood oxygen concentration of the patient. When the blood oxygen concentration of the patient is decreased, the suction tube 113 has to be removed from the tracheostomy tube of the patient immediately so that the oxygen-supply tube 112 can supply oxygen to the patient. Therefore, the operator has to cautiously observe the blood oxygen concentration and move the suction tube 113 at the same time, which is inconvenient to operate and requires an experienced operator.

The present invention is, therefore, arisen to obviate or at least mitigate the above-mentioned disadvantages.

SUMMARY OF THE INVENTION

The main object of the present invention is to provide an intelligent exhaled sputum-suction and inhaled oxygen-supply device to overcome the above-mentioned disadvantages.

To achieve the above and other objects, the present invention provides an intelligent exhaled sputum-suction and inhaled oxygen-supply device, configured to be applied to a respiratory tract of a patient, including: a sputum-suction and oxygen-supply tube unit, a gas-regulating unit and a control unit.

The sputum-suction and oxygen-supply tube unit includes a major oxygen-supply tube and a major sputum-suction tube configured to be disposed through the respiratory tract. The gas-regulating unit includes an oxygen-supply module, a sputum-suction module, a minor oxygen-supply tube communicating the oxygen-supply module with the major oxygen-supply tube, a minor sputum-suction tube communicating the sputum-suction module with the major sputum-suction tube, and a respiration sensor configured to sense a breathing state of the patient. The control unit is electrically connected with the sputum-suction module and the respiration sensor, and the control unit controls the sputum-suction module to draw gas from the minor sputum-suction tube when the respiration sensor senses that the patient is in an exhalation state.

The advantage of the present invention is that: with the configurations of the major oxygen-supply tube, the major sputum-suction tube, the oxygen-supply module, the sputum-suction module and the respiration sensor, the intelligent exhaled sputum-suction and inhaled oxygen-supply device can intelligently supply oxygen and suck sputum according to the breathing state of the patient, so that the patient can inhale oxygen when breathing in and be sucked sputum when breathing out, which simplifies the operating processes.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
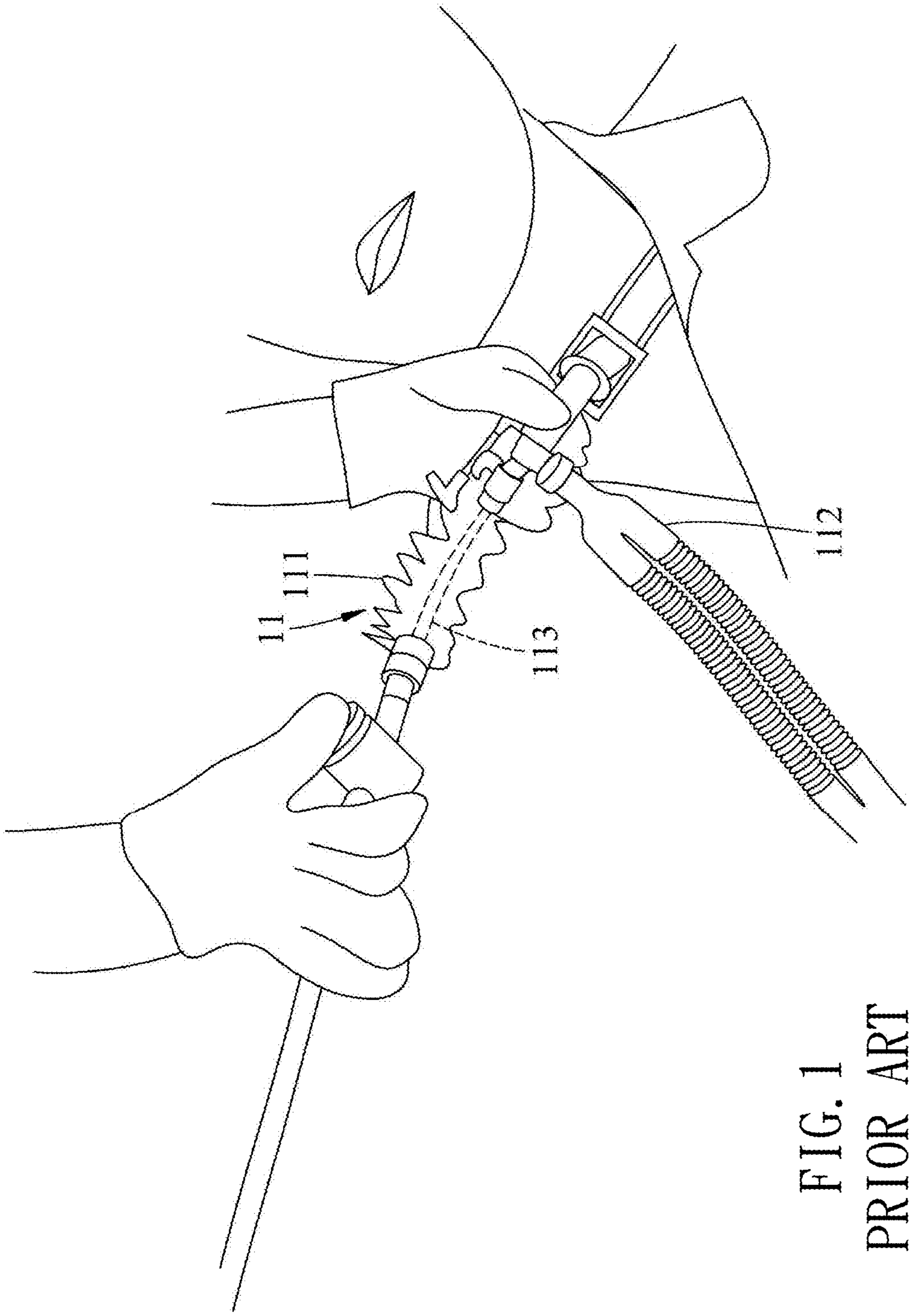
FIG. 1 PRIOR ART
FIG. 1 is a schematic diagram showing operation of a conventional sputum-suction device.
Figure 2:
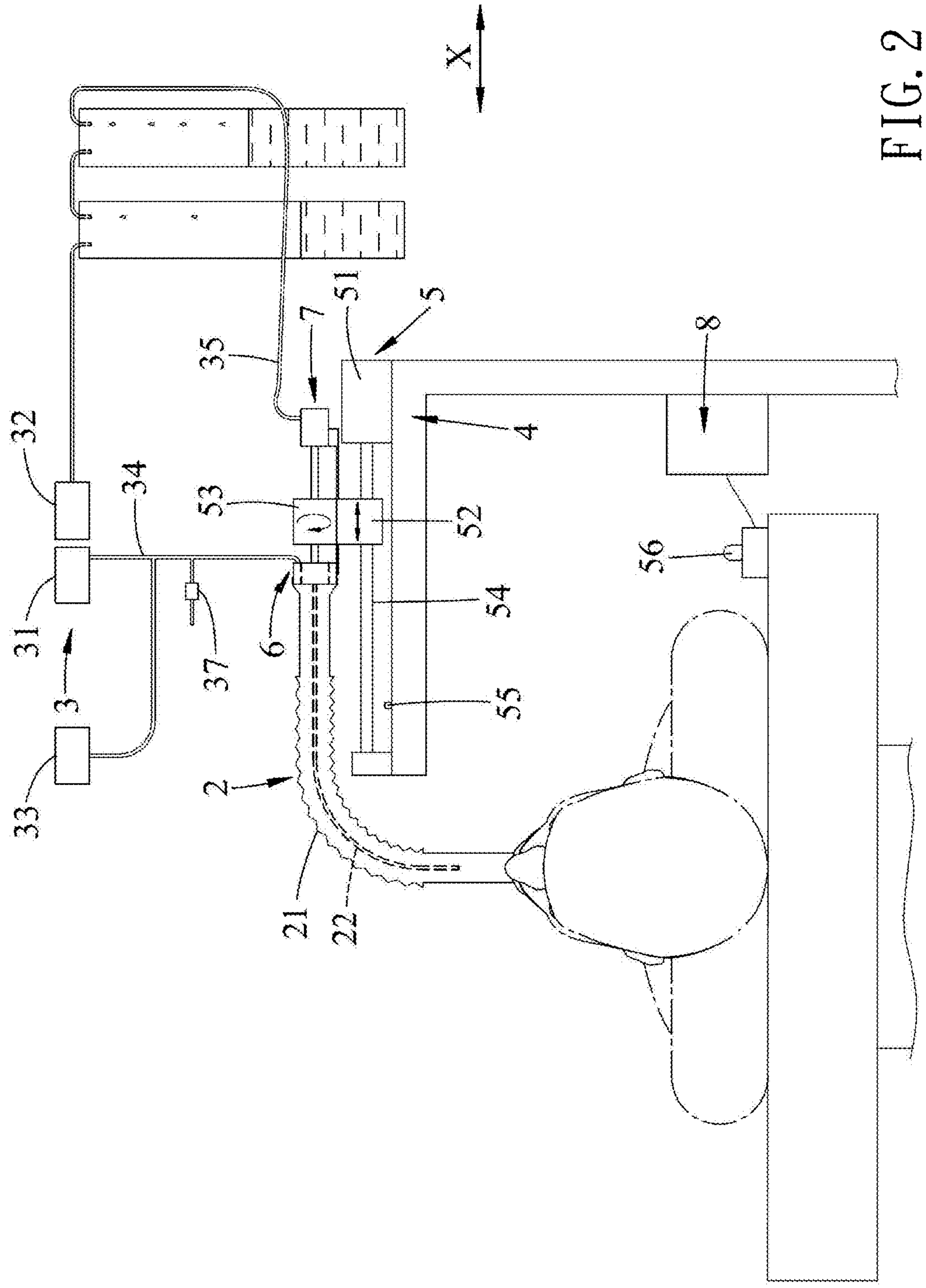
FIG. 2 is a schematic diagram according to a preferable embodiment of the present invention before a major sputum-suction tube is inserted into a respiratory tract of a patient.
Figure 3:
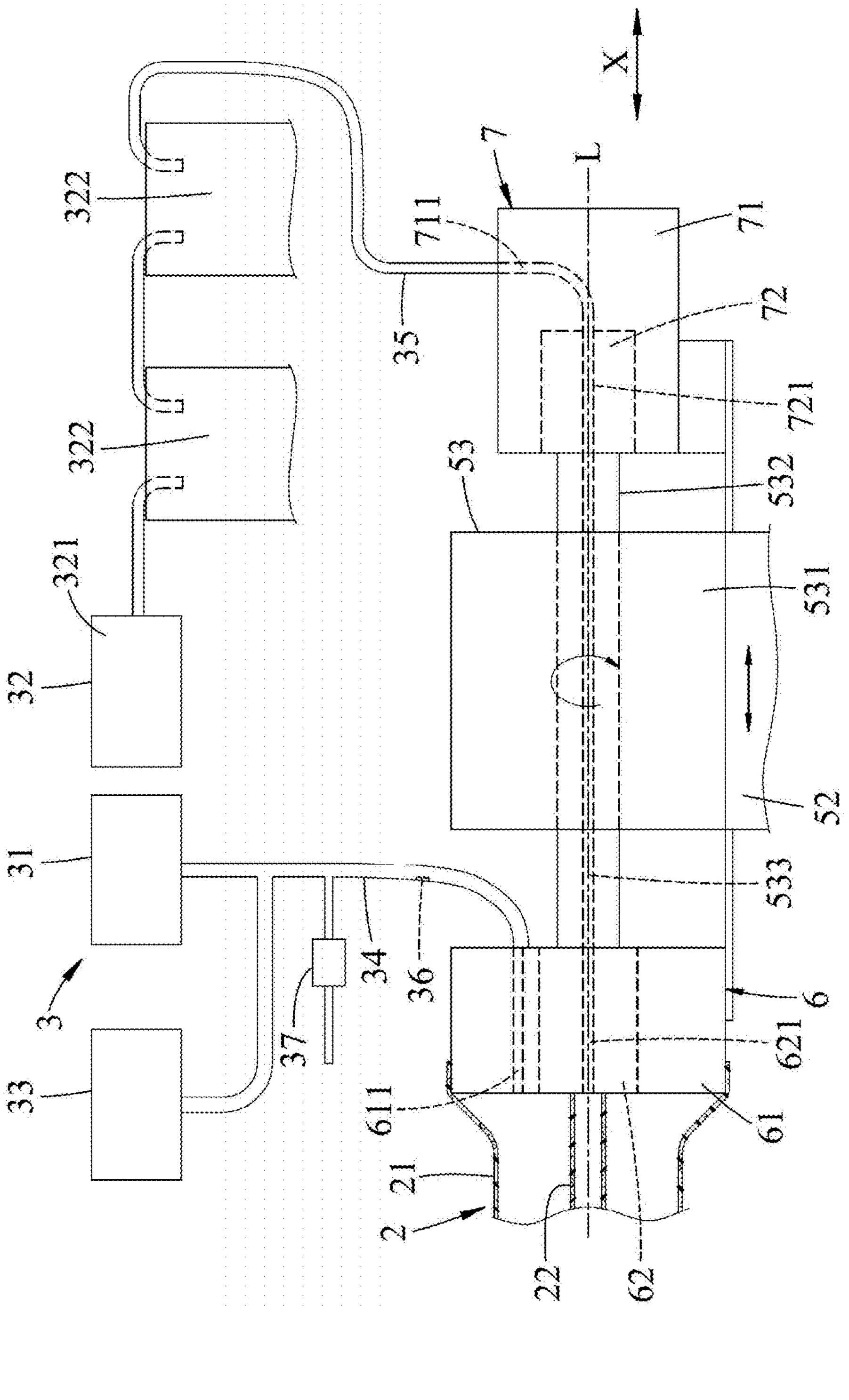
FIG. 3 is a partial enlargement of FIG. 2.
Figure 4:
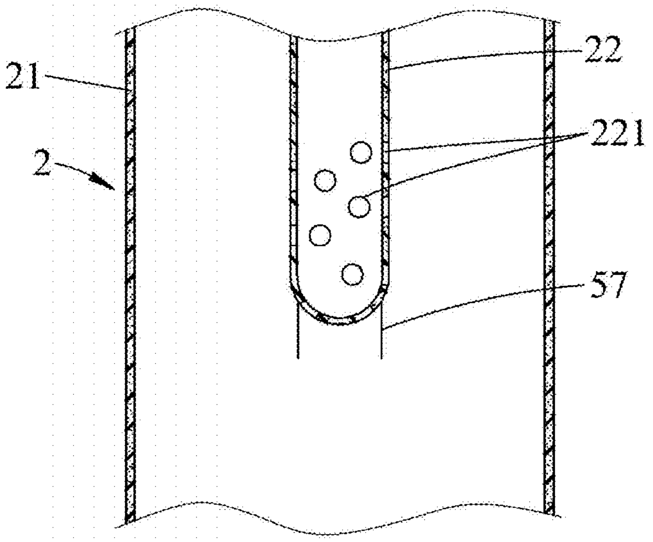
FIG. 4 is a partially enlarged cross-sectional view showing a major oxygen-supply tube, the major sputum-suction tube and a positioning sensor according to a preferable embodiment of the present invention.

Please refer to FIGS. 2 to 4 for a preferable embodiment of the present invention. An intelligent exhaled sputum-suction and inhaled oxygen-supply device of the present invention is configured to be applied to a respiratory tract of a patient, and the intelligent exhaled sputum-suction and inhaled oxygen-supply device includes a sputum-suction and oxygen-supply tube unit 2, a gas-regulating unit 3, a base 4, a driving unit 5, a front adapter unit 6, a rear adapter unit 7 and a control unit 8. In this embodiment, the respiratory tract is a tracheostomy tube of the patient, and the respiratory tract may be the patient's mouth or nostrils in other embodiments.

The sputum-suction and oxygen-supply tube unit 2 includes a major oxygen-supply tube 21 and a major sputum-suction tube 22 configured to be disposed within the respiratory tract, and the major sputum-suction tube 22 includes a plurality of through holes 221. In this embodiment, the major sputum-suction tube 22 is disposed within the major oxygen-supply tube 21, and the major oxygen-supply tube 21 is a retractable tube.

The gas-regulating unit 3 includes an oxygen-supply module 31, a sputum-suction module 32, a gas supply module 33, a minor oxygen-supply tube 34 communicating the oxygen-supply module 31 and the gas supply module 33 with the major oxygen-supply tube 21, a minor sputum-suction tube 35 communicating the sputum-suction module 32 with the major sputum-suction tube 22, a respiration sensor 36 configured to sense a breathing state of the patient, and a one-way input tube 37 communicated with the minor oxygen-supply tube 34. In this embodiment, the gas supply module 33 supplies a gas with 3~5 mmHg pressure, and the one-way input tube 37 is configured to add a medicine spray, steam, or the like. The feature of one-way input is commonly used in the field of the present invention so that its principle will not be further described.

In this embodiment, the respiration sensor 36 is a pressure sensor or a flow sensor disposed in the minor oxygen-supply tube 34 so as to obtain the breathing state of the patient. The pressure sensor may be disposed on other positions communicated with the minor oxygen-supply tube 34. In other embodiments, the respiration sensor 36 may determine the breathing state of the patient by sensing expansion and contraction of the thoracic cavity of the patient, or any other ways that can sense the breathing state of the patient.

The sputum-suction module 32 includes a gas extractor 321 and two filters 322 communicated between the gas extractor 321 and the minor sputum-suction tube 35 and configured to collect the sputum from the patient. The two filter 322 are existing devices used to filter the sputum and will not be further described. The base 4 is arranged adjacent to the patient.

The driving unit 5 includes a first motor 51 disposed on the base 4, a moving platform 52 being drivable to move back and forth in a front-rear direction X by the first motor 51, a second motor 53 disposed on the moving platform 52, a guiding threaded rod 54 screwed with the moving platform 52, a limit switch 55 electrically connected with the first motor 51, an emergency stop button 56, and a positioning sensor 57 disposed on an end of the major sputum-suction tube 22. The guiding threaded rod 54 is drivable by the first motor 51 to rotate and drive the moving platform 52 to move, and the limit switch 55 stops the first motor 51 when the limit switch 55 senses that the moving platform 52 is approaching. In this embodiment, a position of the limit switch 55 is changeable as required so as to restrict a moving distance of the moving platform 52 for safety.

The second motor 53 includes a motor body 531 disposed on the moving platform 52 and a hollow drive shaft 532, and the hollow drive shaft 532 is disposed through the motor body 531 in the front-rear direction X and is drivable by the motor body 531 to rotate about an axis L extending in the front-rear direction X. The hollow drive shaft 532 has a guiding hole 533 extending therethrough. In this embodiment, the second motor 53 is a hollow shaft motor.

The front adapter unit 6 includes a front mounting portion 61 disposed in front of the second motor 53 and a front rotating portion 62 rotatably disposed on the front mounting portion 61 and connected with a front end of the hollow drive shaft 532. The front mounting portion 61 has a front outer connecting hole 611, an end of the front outer connecting hole 611 is open forward, and another end of the front outer connecting hole 611 is connected with the minor oxygen-supply tube 34. The front rotating portion 62 has a front inner connecting hole 621 penetrating therethrough and communicated with the guiding hole 533 and the plurality of through holes 221 of the major sputum-suction tube 22. The major oxygen-supply tube 21 is stretchably sleeved to a front side of the front mounting portion 61, and the major sputum-suction tube 22 is disposed within the major oxygen-supply tube 21 and connected with a front side of the front rotating portion 62 so as to be communicated with the front inner connecting hole 621 and be drivable to rotate with the front rotating portion 62 by the hollow drive shaft 532. The positioning sensor 57 is disposed on an end of the major sputum-suction tube 22 opposite to the front rotating portion 62.

The rear adapter unit 7 includes a rear mounting portion 71 disposed behind the second motor 53 and a rear rotating portion 72 rotatably disposed on a front side of the rear mounting portion 71 and connected with a rear end of the hollow drive shaft 532. The rear mounting portion 71 has a rear outer connecting hole 711, an end of the rear outer connecting hole 711 extends to a rear side of the rear rotating portion 72, and another side of the rear outer connecting hole 711 is connected with the minor sputum-suction tube 35. The rear rotating portion 72 has a rear inner connecting hole 721 communicated with the guiding hole 533 and the rear outer connecting hole 711, and the minor sputum-suction tube 35 is communicated with the guiding hole 533 through the rear outer connecting hole 711 and the rear inner connecting hole 721.

The control unit 8 is electrically connected with the sputum-suction module 32, the respiration sensor 36, the first motor 51, the second motor 53, the emergency stop button 56 and the positioning sensor 57. The control unit 8 controls the first motor 51 and the second motor 53 to drive the major sputum-suction tube 22 to move and rotate. In this embodiment, when the emergency stop button 56 is triggered, the control unit 8 controls the first motor 51 and the second motor 53 to stop to protect the patient. In this embodiment, the positioning sensor 57 and the control unit 8 are connected with each other by a rotary electrical connector so as to keep electrical connection when the positioning sensor 57 is driven to rotate. The feature of electrical connection is commonly used in the field of the present invention and will not be further described.

The control unit 8 determines that the patient is in an inspiratory state when the respiration sensor 36 senses a negative airway pressure or an inhaled flow, and the control unit 8 determines that the patient is in an exhalation state when the respiration sensor 36 senses a positive gas pressure. The control unit 8 controls the sputum-suction module 32 to draw gas from the minor sputum-suction tube 35 when the respiration sensor 36 senses that the patient is in the exhalation state. The control unit 8 may control the oxygen-supply module 31 to supply oxygen through the oxygen-supply tube 34 when the respiration sensor 36 senses that the patient is in the inspiratory state.

When the hollow drive shaft 532 of the second motor 53 is driven to rotate by the motor body 531, the front rotating portion 62 and the rear rotating portion 72 are driven to rotate and drive the major sputum-suction tube 22 to rotate. When the first motor 51 drives the guiding threaded rod 54 to rotate and drive the moving platform 52 to move, the major oxygen-supply tube 21 is stretched or compressed, and the major sputum-suction tube 22 is moved.

Figure 5:
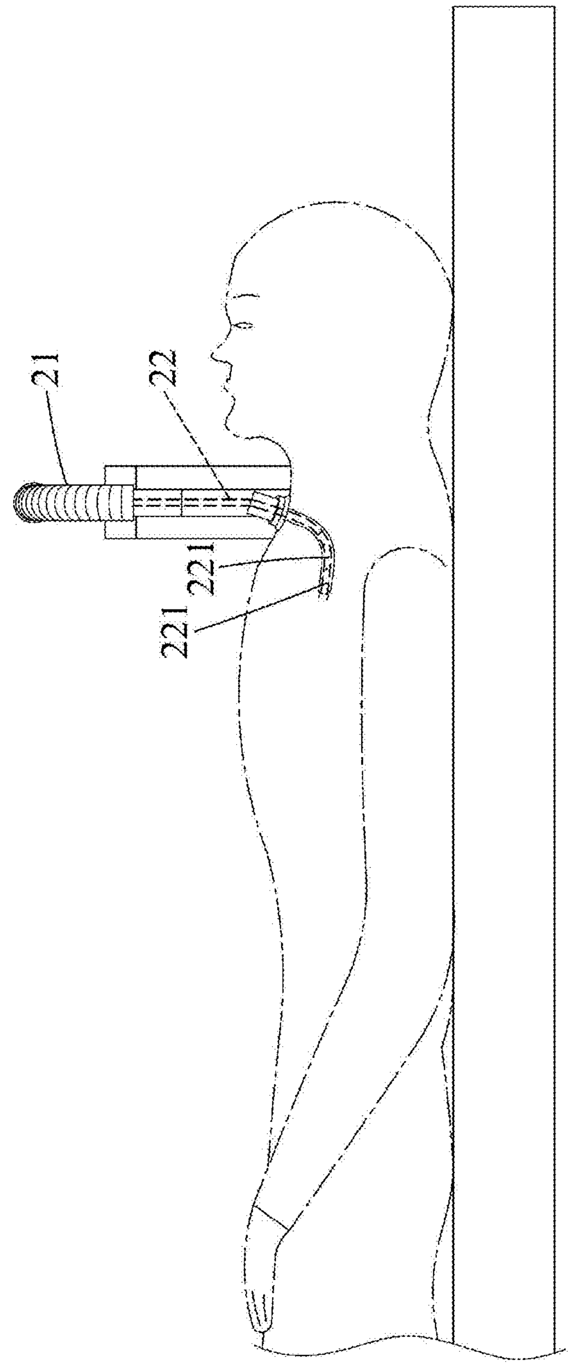
FIG. 5 is a schematic diagram according to a preferable embodiment of the present invention when the major sputum-suction tube is disposed within the respiratory tract of the patient.

Please refer to FIGS. 2, 4 and 5, in operation, the major oxygen-supply tube 21 is disposed into the respiratory tract of the patient (as shown in FIG. 2), and the major sputum-suction tube 22 is located out of the respiratory tract. Then, the control unit 8 controls the first motor 51 and the second motor 52 to operate and the major sputum-suction tube 22 is rotatably disposed into the respiratory tract of the patient (as shown in FIG. 5). At this time, the major oxygen-supply tube 21 is gradually compressed and an inner channel of the major oxygen-supply tube 21 is unobstructed. Since the major sputum-suction tube 22 keeps rotating, the sputum is scraped and adheres to an end of the major sputum-suction tube 22 having the plurality of through holes 221. The control unit 8 controls the first motor 51 and the second motor 52 to stop when the positioning sensor 57 senses an obstacle (such as bronchus). In this embodiment, the positioning sensor 57 includes three fiber tactile sensors (such as Von Frey Filaments).

Figure 6:
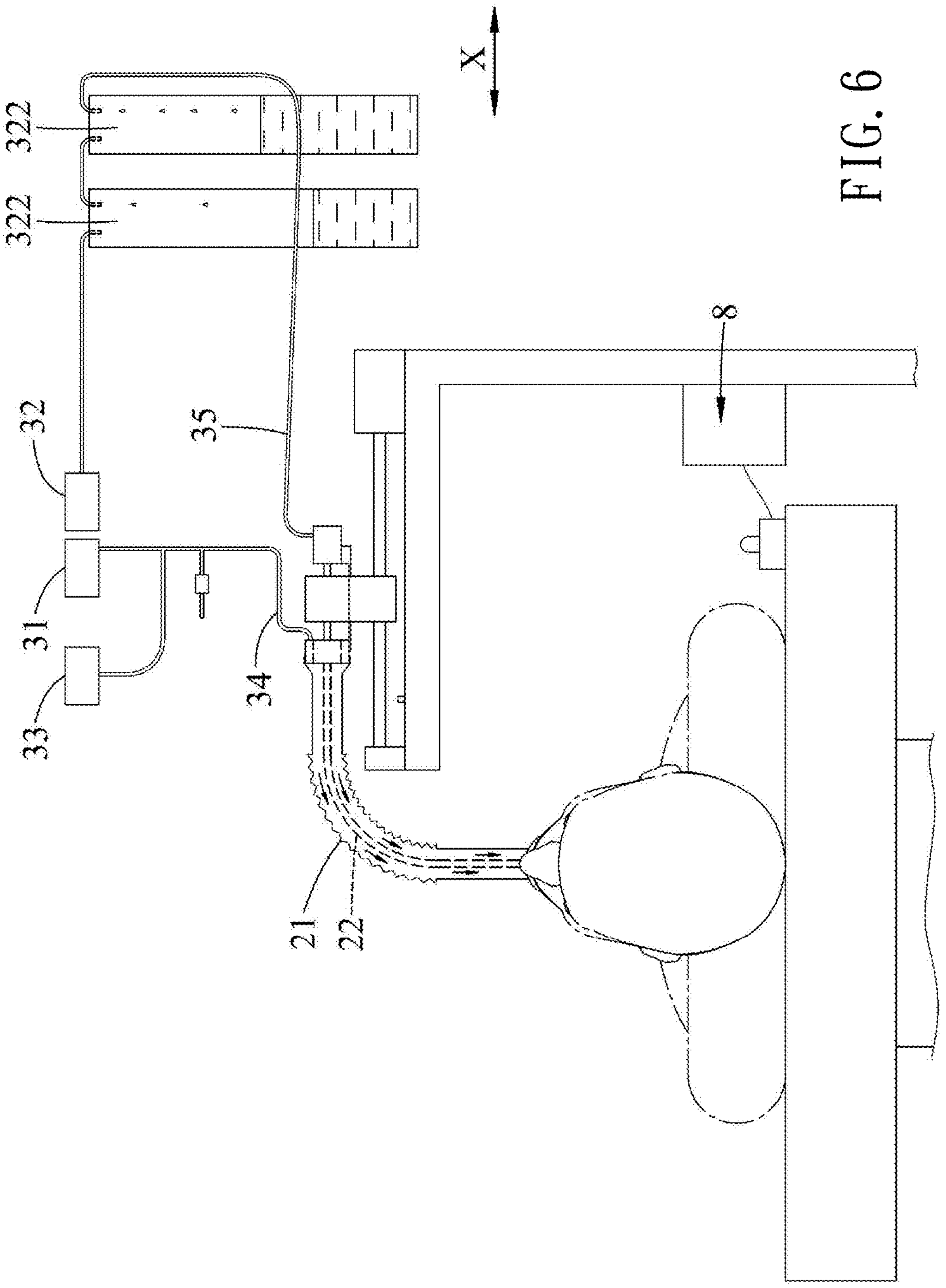
FIG. 6 is a schematic diagram according to a preferable embodiment of the present invention when the major sputum-suction tube is disposed within the respiratory tract of the patient and the major oxygen-supply tube is supplying oxygen.

Please refer to FIGS. 3, 5 and 6, in this process, the oxygen-supply module 31 supplies oxygen to the minor oxygen-supply tube 34 continuously, and the gas supply module 33 supplies the gas pressure continuously so that the patient can inhale oxygen (as the arrows indicated in FIG. 6).

Figure 7:
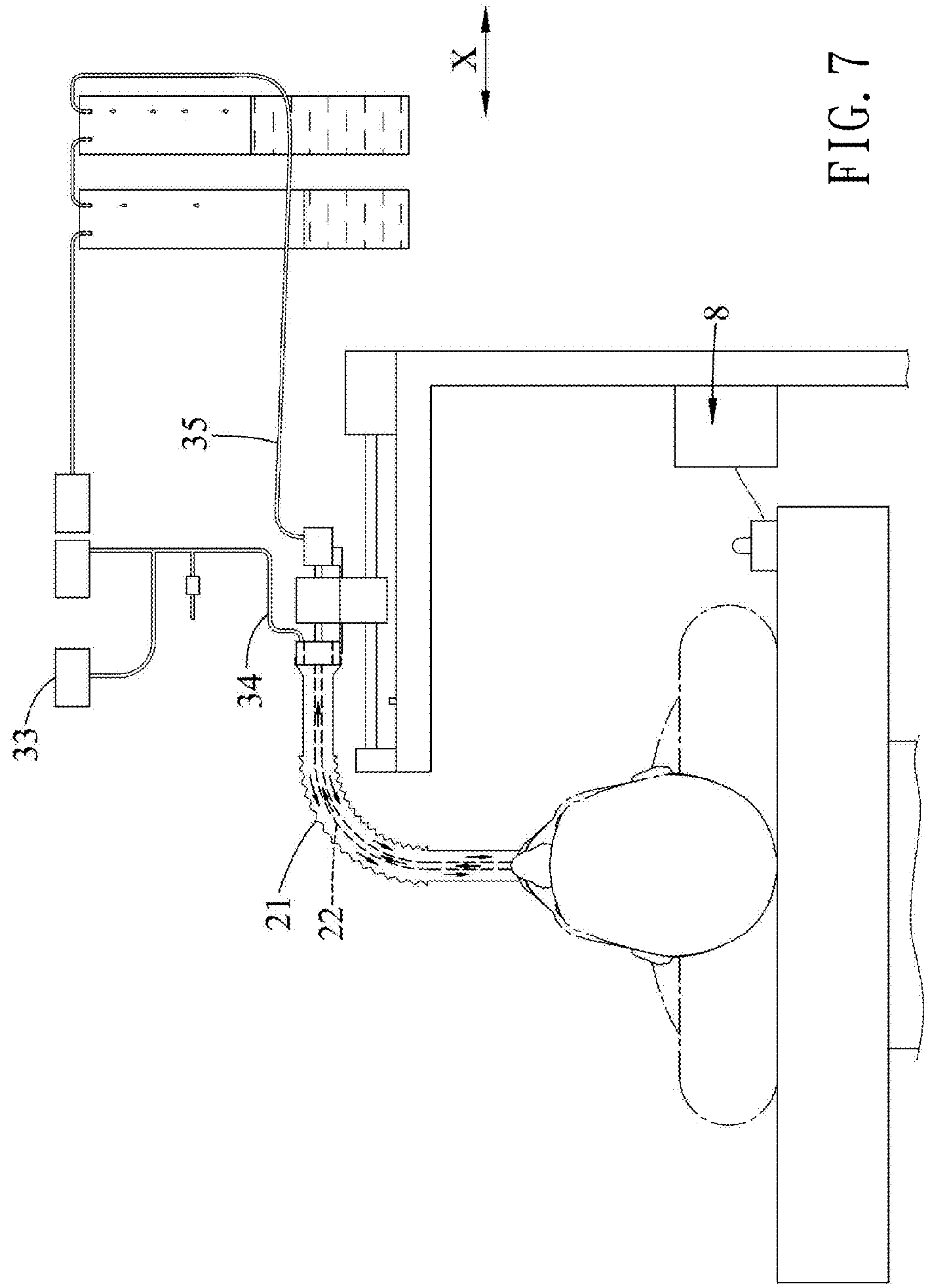
FIG. 7 is a schematic diagram according to a preferable embodiment of the present invention when the major sputum-suction tube is disposed within the respiratory tract of the patient and the major sputum-suction tube is sucking sputum.

Please refer to FIGS. 3, 5 and 7, when the control unit 8 determines that the patient is in the exhalation state, the gas supplied by the gas supply module 33 can keep the respiratory tract of the patient unobstructed. Therefore, the sputum can be sucked by the minor sputum-suction tube 35 and collected to the two filters 322 through the plurality of through holes 221, the front inner connecting hole 621, the guiding hole 533, the rear inner connecting hole 721, the rear outer connecting hole 711 and the minor sputum-suction tube 35 in sequence.

The whole sputum suction process of the present invention is carried out by an intelligent procedure, which largely reduces the operating processes and the technical requirements of the operator.

In other embodiments, the intelligent exhaled sputum-suction and inhaled oxygen-supply device may be configured without the driving unit 5, the front adapter unit 6 and the rear adapter unit 7, the major oxygen-supply tube 21 are separated from the major sputum-suction tube 22, and the major oxygen-supply tube 21 and the major sputum-suction tube 22 are respectively connected with the minor oxygen-supply tube 34 and the minor sputum-suction tube 35. In operation, the major oxygen-supply tube 21 and the major sputum-suction tube 22 may be disposed within the patient' mouth or nostrils, and the oxygen-supply module 31 supplies oxygen continuously. The control unit 8 intelligently determines the breathing state of the patient, and the position of the major sputum-suction tube 22 is adjustable manually. Since the operator does not need to observe the blood oxygen concentration of the patient, the effect of reducing the technical requirements of the operator is also achieved.

Figure 8:
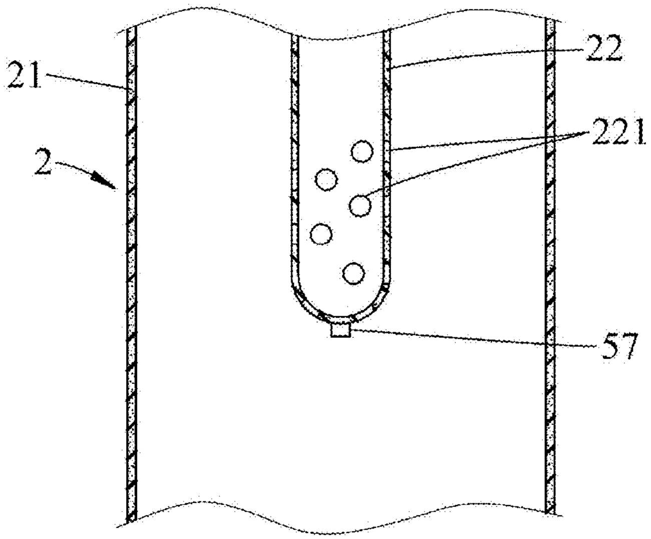
FIG. 8 is a partially enlarged cross-sectional view showing the major oxygen-supply tube, the major sputum-suction tube and the positioning sensor according to another preferable embodiment of the present invention.

Please refer to FIG. 8, showing another embodiment of the present invention. The positioning sensor 57 may be a resistance sensor, an optical sensor or a magnetic sensor which also provides distance sensing effect.

In summary, with the configurations of the major oxygen-supply tube 21, the major sputum-suction tube 22, the oxygen-supply module 31, the sputum-suction module 32 and the respiration sensor 36, the intelligent exhaled sputum-suction and inhaled oxygen-supply device can intelligently supply oxygen, and the control unit 8 intelligently sucks sputum according to the breathing state of the patient. Therefore, the patient can inhale oxygen when breathing in and be sucked sputum when breathing out, which simplifies the operating processes.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An intelligent exhaled sputum-suction and inhaled oxygen-supply device, configured to be applied to a respiratory tract of a patient, including:

a sputum-suction and oxygen-supply tube unit, including a major oxygen-supply tube and a major sputum-suction tube configured to be disposed within the respiratory tract;

a gas-regulating unit, including an oxygen-supply module, a sputum-suction module, a minor oxygen-supply tube communicating the oxygen-supply module with the major oxygen-supply tube, a minor sputum-suction tube communicating the sputum-suction module with the major sputum-suction tube, and a respiration sensor configured to sense a breathing state of the patient; and a control unit, electrically connected with the sputum-suction module and the respiration sensor, the control unit configured to controll the sputum-suction module to draw gas from the minor sputum-suction tube when the respiration sensor senses that the patient is in an exhalation state;

wherein the respiration sensor is a pressure sensor or a flow sensor, and the control unit is configured to determines that the patient is in an inspiratory state when the respiration sensor senses a negative airway pressure or an inhaled flow;

wherein the intelligent exhaled sputum-suction and inhaled oxygen-supply device further includes a base, a driving unit and a front adapter unit, the driving unit includes a first motor, a moving platform and a second motor, the first motor is disposed on the base and electrically connected with the control unit, the moving platform is drivable by the first motor to move back and forth in a front-rear direction, the second motor is electrically connected with the control unit, the second motor includes a motor body disposed on the moving platform and a hollow drive shaft, the hollow drive shaft is disposed through the motor body in the front-rear direction and is drivable by the motor body to rotate about an axis extending in the front-rear direction, the hollow drive shaft has a guiding hole extending therethrough, the front adapter unit includes a front mounting portion disposed in front of the second motor and a front rotating portion rotatably disposed on the front mounting portion and connected with a front end of the hollow drive shaft, the front mounting portion has a front outer connecting hole, an end of the front outer connecting hole is open forward, another end of the front outer connecting hole is connected with the minor oxygen-supply tube, the front rotating portion has a front inner connecting hole penetrating therethrough and communicated with the guiding hole, the major oxygen-supply tube is stretchably sleeved to a front side of the front mounting portion, the major sputum-suction tube is disposed within the major oxygen-supply tube and connected to a front side of the front rotating portion so as to be communicated with the front inner connecting hole and be drivable to rotate with the front rotating portion by the hollow drive shaft, and the control unit is configured to control the first motor and the second motor to drive the major sputum-suction tube to move and rotate.

2. The intelligent exhaled sputum-suction and inhaled oxygen-supply device of claim 1, wherein the sputum-suction module includes a gas extractor and at least one filter, and the at least one filter is communicated between the gas extractor and the minor sputum-suction tube and configured to collect sputum from the patient.

3. The intelligent exhaled sputum-suction and inhaled oxygen-supply device of claim 1, further including a rear adapter unit, wherein the rear adapter unit includes a rear mounting portion disposed behind the second motor and a rear rotating portion rotatably disposed on a front side of the rear mounting portion and connected with a rear end of the hollow drive shaft, the rear mounting portion has a rear outer connecting hole, an end of the rear outer connecting hole extends to a rear side of the rear rotating portion, another side of the rear outer connecting hole is connected with the minor sputum-suction tube, the rear rotating portion has a rear inner connecting hole communicated with the guiding hole and the rear outer connecting hole, and the minor sputum-suction tube is communicated with the guiding hole through the rear outer connecting hole and the rear inner connecting hole.

4. The intelligent exhaled sputum-suction and inhaled oxygen-supply device of claim 1, wherein the driving unit further includes a guiding threaded rod screwed with the moving platform and a limit switch electrically connected with the first motor, the guiding threaded rod is drivable by the first motor to rotate and drive the moving platform to move, and the limit switch is configured to stops the first motor when the limit switch senses that the moving platform is approaching.

5. The intelligent exhaled sputum-suction and inhaled oxygen-supply device of claim 1, wherein the driving unit further includes an emergency stop button electrically connected with the control unit.

6. The intelligent exhaled sputum-suction and inhaled oxygen-supply device of claim 1, wherein the major sputum-suction tube includes a plurality of through holes communicated with the front inner connecting hole.

7. The intelligent exhaled sputum-suction and inhaled oxygen-supply device of claim 1, wherein the driving unit further includes a positioning sensor electrically connected with the control unit and disposed on an end of the major sputum-suction tube opposite to the front rotating portion, and the control unit is configured to controls the first motor and the second motor to stop when the positioning sensor senses an obstacle.

8. The intelligent exhaled sputum-suction and inhaled oxygen-supply device of claim 1, wherein the gas-regulating unit further includes a gas supply module communicated with the minor oxygen-supply tube.

9. The intelligent exhaled sputum-suction and inhaled oxygen-supply device of claim 1, wherein the gas-regulating unit further includes a one-way input tube communicated with the minor oxygen-supply tube.

* * * * *